(12) United States Patent
Golden

(10) Patent No.: US 8,783,992 B2
(45) Date of Patent: Jul. 22, 2014

(54) SHUTTER REPAIR SYSTEM

(71) Applicants: Ben Hoch, Irvine, CA (US); Michael Cerillo, San Clemente, CA (US)

(72) Inventor: Henry Golden, Irvine, CA (US)

( * ) Notice: Subject to any disclaimer, the term of this patent is extended or adjusted under 35 U.S.C. 154(b) by 0 days.

(21) Appl. No.: 13/948,079

(22) Filed: Jul. 22, 2013

(65) Prior Publication Data

US 2013/0308998 A1 Nov. 21, 2013

Related U.S. Application Data

(63) Continuation of application No. 13/032,852, filed on Feb. 23, 2011.

(60) Provisional application No. 61/338,902, filed on Feb. 26, 2010.

(51) Int. Cl.
*F16D 3/00* (2006.01)

(52) U.S. Cl.
USPC .............................................. 403/57; 49/74.1

(58) Field of Classification Search
USPC ...................... 403/53, 57, 207; 49/74.1, 87.1; 160/178.3, 174 R, 178.1 R, 84.04
See application file for complete search history.

(56) References Cited

U.S. PATENT DOCUMENTS

| | | | | |
|---|---|---|---|---|
| 272,914 A | * | 2/1883 | Soule | 49/74.1 |
| 633,013 A | * | 9/1899 | Kooy | 49/74.1 |
| 1,340,252 A | * | 5/1920 | Rasmussen | 49/74.1 |
| 4,154,281 A | * | 5/1979 | Schluep | 160/178.3 |
| 4,655,003 A | * | 4/1987 | Henley, Sr. | 49/87.1 |
| 5,020,276 A | * | 6/1991 | Zittell | 49/87.1 |
| 5,303,507 A | * | 4/1994 | Oille | 49/74.1 |

* cited by examiner

*Primary Examiner* — Michael P Ferguson
*Assistant Examiner* — Daniel Wiley
(74) *Attorney, Agent, or Firm* — Plager Schack LLP

(57) ABSTRACT

A system is provided for joining two discrete devices together, such as a louver panel and a tilt rod, where the system comprises a first and second component, each comprising a link connected to a resilient sheet, with each component being independently adhered to one of the two discrete devices for joining the two devices in engaged but moveable relationship.

1 Claim, 5 Drawing Sheets

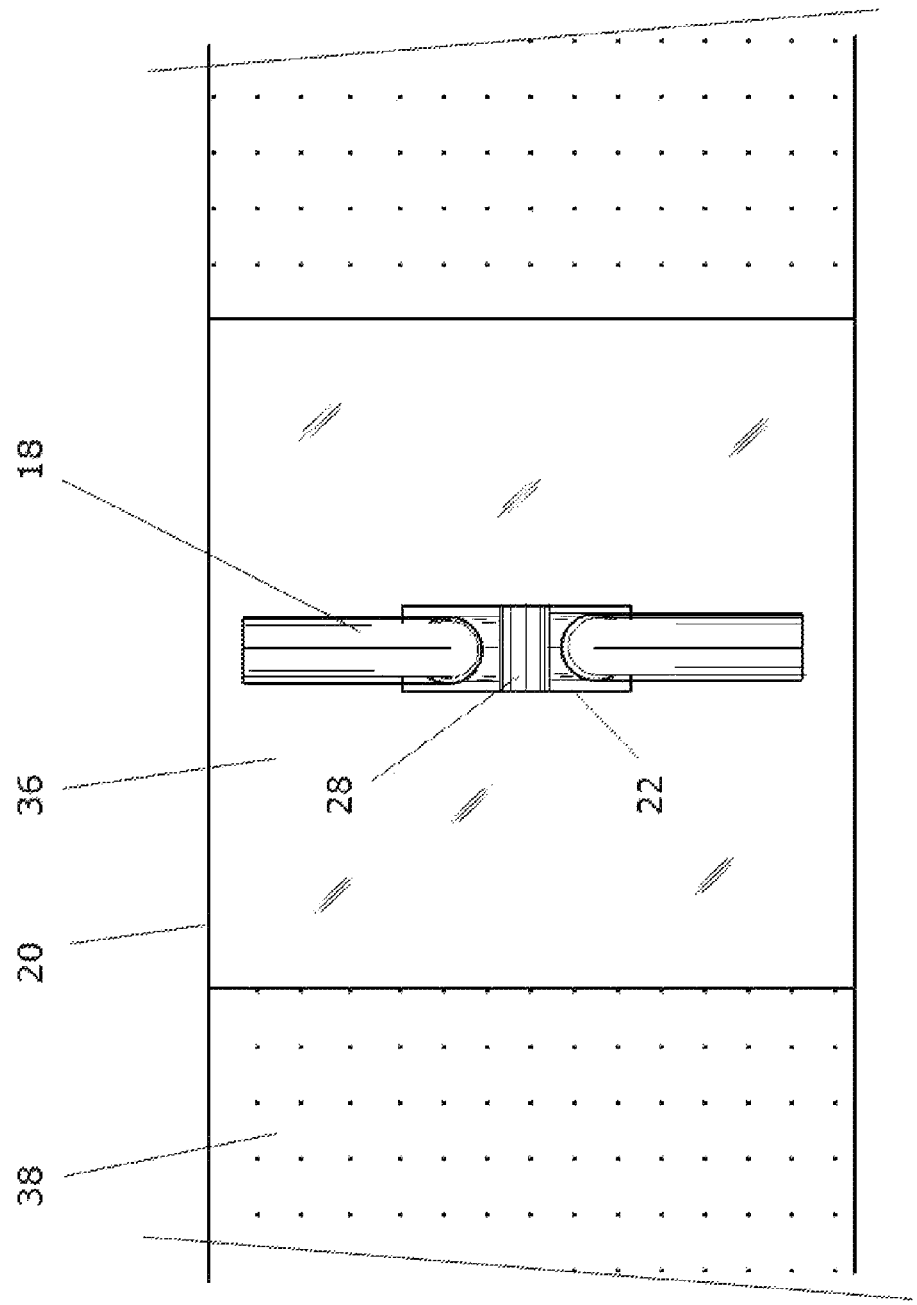

SHUTTER REPAIR SYSTEM

CROSS-REFERENCE TO RELATED APPLICATIONS

This application is based on and claims priority to U.S. Provisional Patent Application No. 61/338,902, filed on Feb. 26, 2010, and entitled "SHUTTER REPAIR ASSEMBLY," the entire contents of which is hereby expressly incorporated by reference.

BACKGROUND

The present invention relates generally to repairing solid window coverings, and more specifically to a system for repairing shutter louvers and other similar devices, as well as joining two discrete members together in linked by moveable engagement.

Numerous homes and offices are covered (or treated) with solid window coverings, such as louvered shutters. A louvered shutter generally consists of a number of louvers or slats that when turned in position almost entirely block light and when turned in an different position permit almost entire visibility through the window, with numerous adjustable positions therebetween. The advantage of such an arrangement is that it permits the user to control the amount of light entering a room fairly easily by adjusting one or more tilt rods connected to all of the louver panels collectively. With many louvered shutters, the louver panels are positioned horizontally, with the tilt rod(s) or shutter rods positioned vertically. The user may grab the tilt rod and raise it upwardly or downwardly, opening or closing the louver panels, respectively. Louvered shutters come in many different materials, including wood, plastic and metal.

Typically, louvered panels are connected to tilt rods via a mechanism that permits movement of the panels relative to the shudder rod. In many cases, the mechanism is a pair of engaged links, each connected to the tilt rod and the other connected to the louver panel. The links may be annular rings, or some other mechanism that permits secure engagement of the pair of links during movement of the rod in a vertical direction.

One of the difficulties with louvered shutters is encountered when one or more of the louver panels becomes detached from the adjustment rod. Although the louver panels are also supported from above (and to each other) by multiple tethers, adjustability of the panels depends upon the movement of the rod vertically, not the tether. So when one or more panels becomes detached from the tilt rod, it remains fairly still when the tilt rod is moved, leaving an unaesthetic and not-fully-functioning window treatment. Detachment often arises when the pair of links becomes either disengaged to each other, or one of the links detaches from the panel or the rod. Although repair kits and devices are available, they do not provide a quick fix that would permit a user to continue to enjoy the benefit of light control with minimal effort. The space that exists between the panels and the rod is quite small, so there is often insufficient room to reattach the links to each other or reattach one of the detached links to the panel or rod. Removal of the entire rod may be necessary in some cases. Moreover, there is risk of ruining the louver panel, which would require replacement of the panel, an even more difficult situation.

Thus, a more efficient and aesthetic system for repairing louvered shutters and other such mechanisms is needed.

SUMMARY

Embodiments of the present invention satisfy at least the need for more efficient and aesthetic louvered shutter repair. In that regard, at least some of the embodiments described herein comprises a dual-component system, with one component configured to adhere to a louver panel and the other component configured to adhere to a tilt rod. The first component is linked to the second component such that a disconnected louver panel is reconnected to the tilt rod to resume control of the panel by the rod. The first and second components each comprise generally a sturdy linking member and a sheet through which the linking member is positioned to permit facile attachment to either the louver panel or tilt rod. The linking members of both components are interlinked so that attachment of both components to the panel and rod joins the panel and rod in a functioning manner. In one embodiment, facile attachment of the components to the louver panel or tilt rod is accomplished using an adhesive.

BRIEF DESCRIPTION OF THE FIGURES

The detailed description of some embodiments of the invention will be is made below with reference to the accompanying figures, wherein like numerals represent corresponding parts of the figures.

FIG. 3 is a schematic view of one component of the dual-component system of the embodiment of FIG. 1;

DETAILED DESCRIPTION OF CERTAIN EMBODIMENTS

Figure 1:
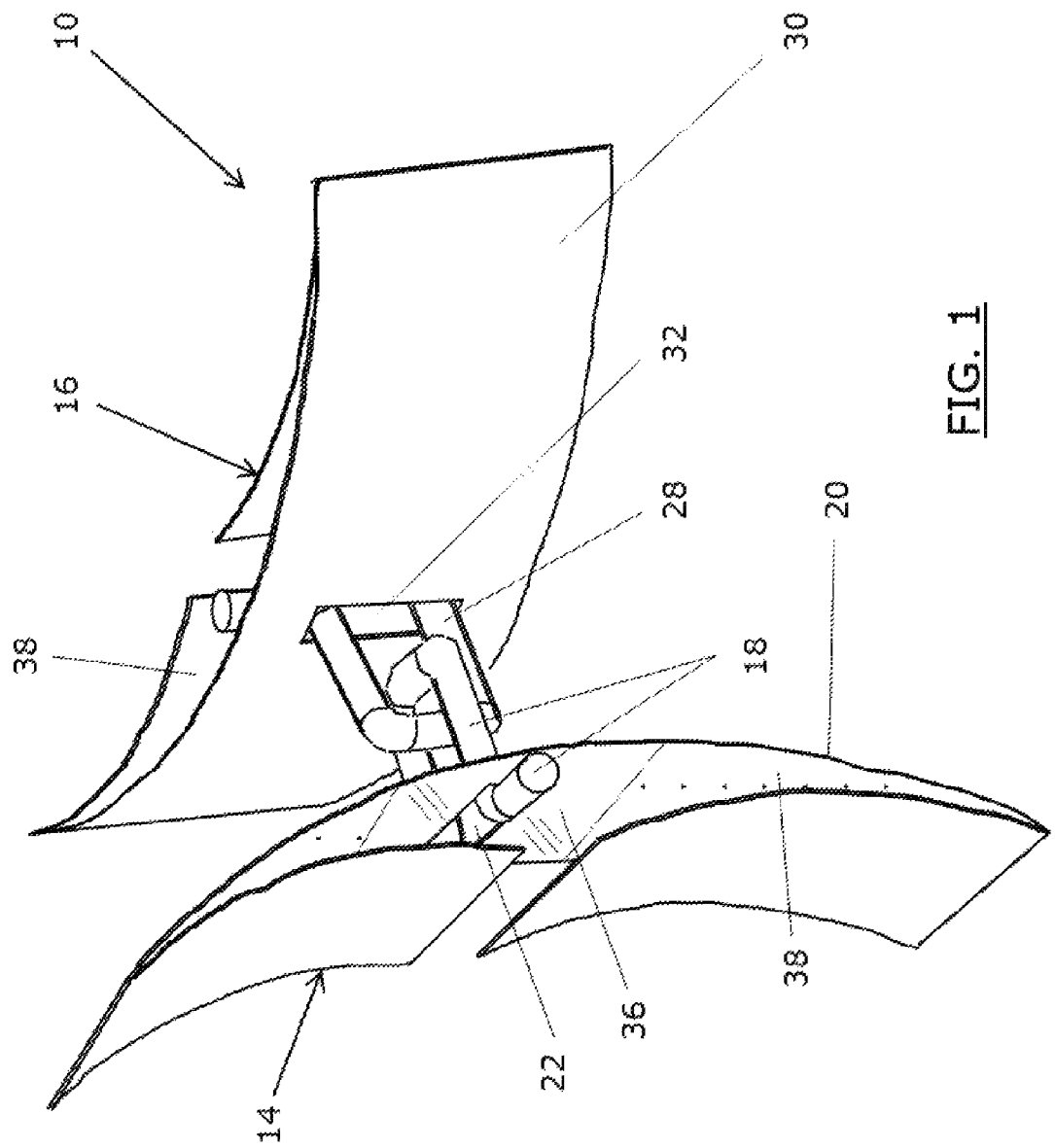
FIG. 1 is a schematic perspective view of one embodiment of the present invention.

Referring to FIG. 1, one embodiment contemplated by the present invention comprises a system 10 that comprises a first component 14 and a second component 16. In the embodiment of FIG. 1, the first and second components 14, 16 are configured similarly, with one usable with a louver panel and one usable with a tilt rod, for example. While application to a window shutter is described for purposes of appreciating the function of the embodiments herein, the embodiments may be used to movable join any two devices for which relative but joined movement is desired. Depending on the application desired, the first and second component may be similarly configured, or they may be tailored more specifically to conform to whatever two devices a user desires to connect using the system herein.

With the embodiment of FIG. 1, the first component 14 comprises a first link 18 having a generally U-shaped rod configuration with orthogonal extensions at the ends, and further comprises a first resilient sheet member 20. The orthogonal extensions of the U-shaped first link 18 project through an opening 22 in the sheet member 20 so that the link is preferably positioned transverse the width of the sheet, although other orientations are contemplated for effective use. The orthogonal extensions of the U-shaped link 18 permit a user to apply force to the first link 18 by pulling at the first sheet 20 in a direction opposite of second component 16.

Like first component 14, the second component 16 comprises a second link 28 penetrating a second resilient sheet member 30 through opening 32 in a transverse orientation relative to the sheet member 30. Advantageously, first and second links 18, 28 are engaged to each other in an orthogonal arrangement (i.e., one horizontal and one vertical). One can appreciate the relative position of the links by referring specifically to FIG. 2. The link 18 may comprise a rod or a plate configured into any geometric shape that permits engagement of link 18 to link 28, as well as respective engagement of link 18 to sheet 20 and link 28 to sheet 30.

As with the structure of the first component 14, a user may apply force to the second link 28 by pulling on the second sheet member 30 in a direction opposite first component 14. Applying opposite forces to the first and second sheet members 20, 30 results in tight engagement of the first and second links 18, 28 in a secure manner. With such an arrangement, it can be appreciated that whatever devices the first and second components are attached to, respectively, will become movably engaged.

Figure 2:
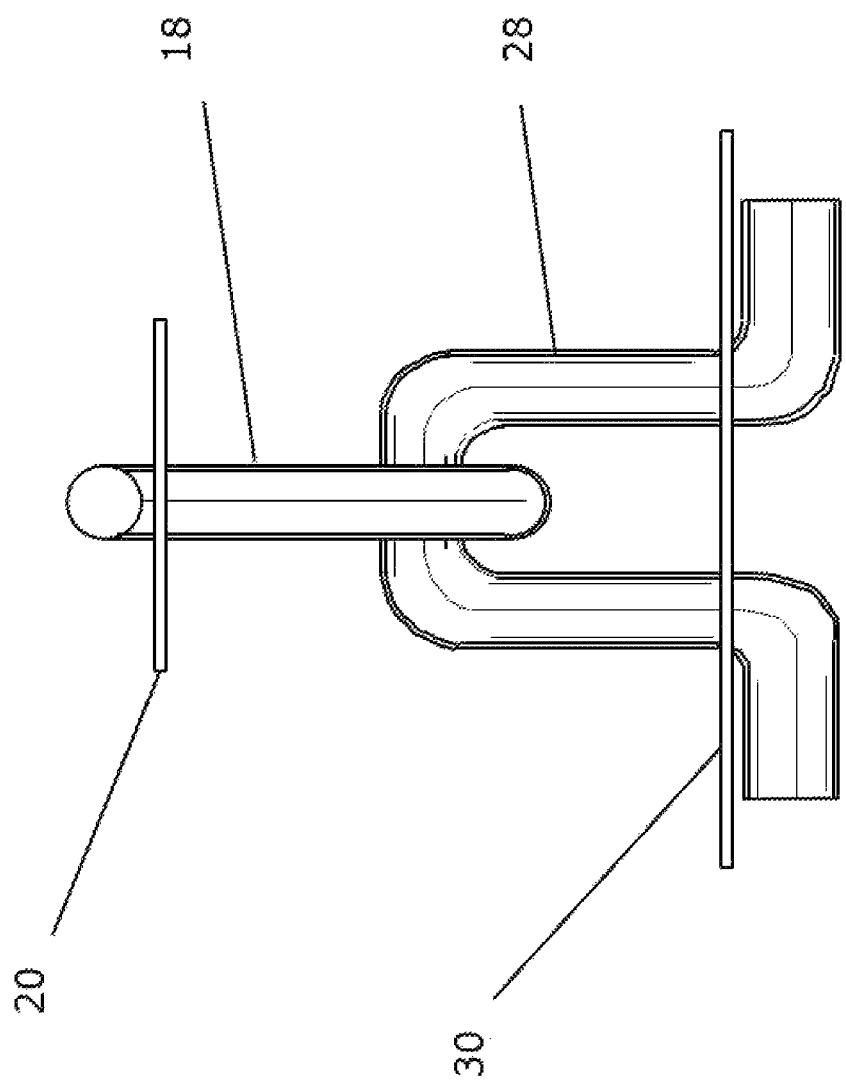
FIG. 2 is a schematic view from a different angle of the embodiment of FIG. 1.

Referring to FIG. 3, to permit ready attachment of the first and second components 14, 16 to discrete devices, the first and second sheet members 20, 30 are configured with resilient but strong material and a means for attaching the members 20, 30 to respective devices. In the embodiment of FIGS. 1 through 3, attachment means comprises an adhesive 38 provided on a front side of sheet 20, with a protective membrane 36 positioned about the orthogonal extensions of the link 18. By avoiding adhesive 38 immediately adjacent the link 18, the link will retain freedom to rotate a bit as necessary when applied to join two discrete devices. The type of adhesive and protective membrane is not critical, and may be selected depending upon the type of application contemplated. The protective membrane 36 provides optional reinforcing capability to resist forces placed on the system when in use.

Figure 4A:
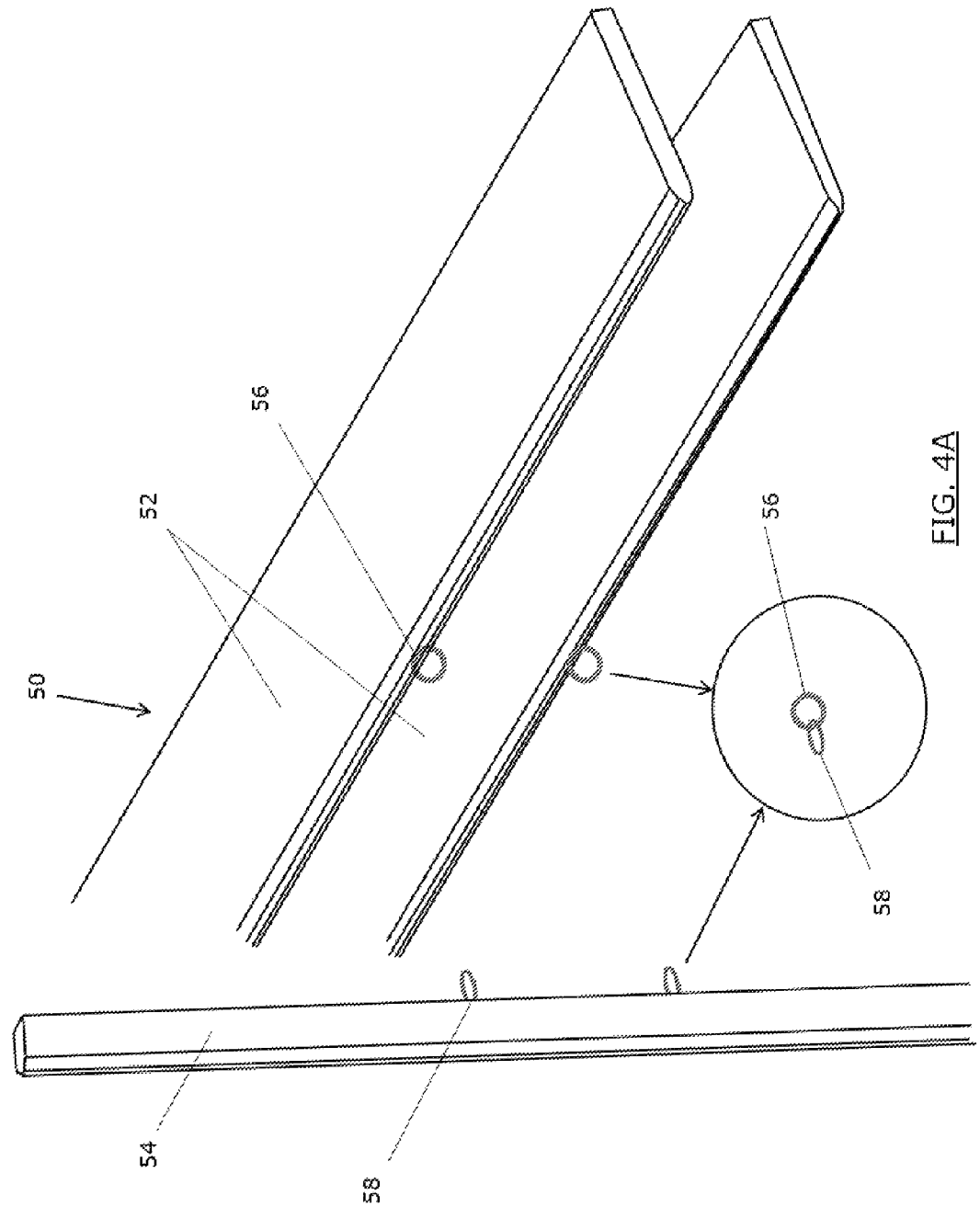
FIG. 4A is a schematic view of a conventional louvered shutter with conventional means of attaching the shutter panels to a tilt rod.
Figure 4B:
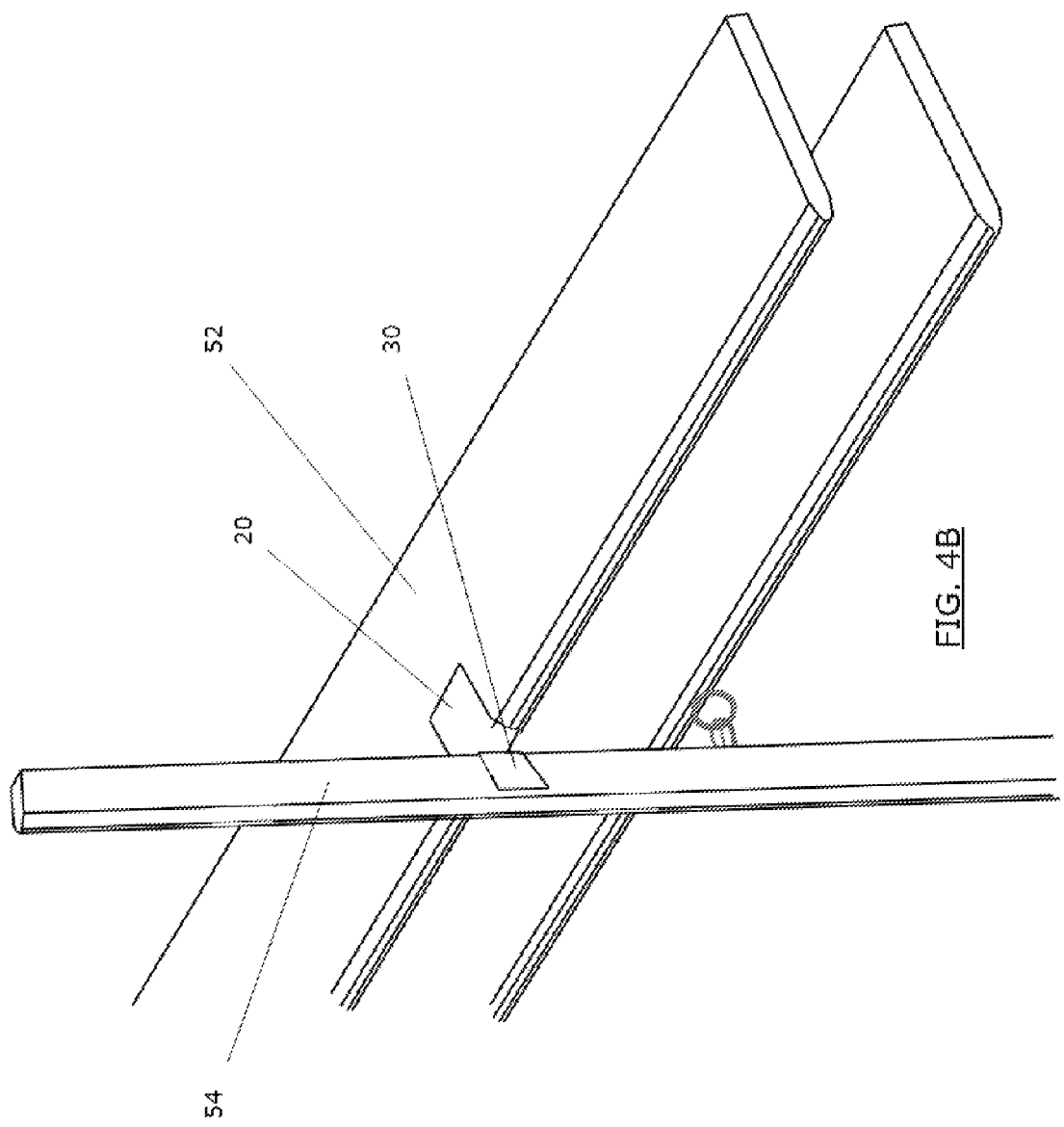
FIG. 4B is a schematic view of the shutter of FIG. 4A showing the embodiment of FIG. 1 applied to the shutter in place of a broken connection.

Referring to FIGS. 4A and 4B, application of one embodiment of the present invention to, for example, a louvered shutter, may be described. In FIG. 4A, a conventional louvered shutter 50 is shown partially comprising a plurality of louver panels 52 and a tilt rod 54. Attached to a central portion of each louver panel is a ring mechanism 56. Attached to corresponding positions on the tilt rod 54 are a set of ring mechanisms 58 configured to securely engage the ring mechanisms 56 of the louver panels, as shown in the small detail provided in FIG. 4A. In normal working configuration, each louver panel is movably engaged to the tilt rod via a pair of linked ring mechanisms 56, 58. In the event that one of the ring link pairs either disengages from each other or on of the ring links disengages from the panel 52 or rod 54, that tilt rod can no longer control movement of the panel. As one can appreciate from FIG. 4B, the space between the tilt rod 54 and the panels 52 is small, so there is not a great deal of working room to repair the disengaged pair of ring links 56, 58. One application of one embodiment of the present invention provides a simple and easy way to repair the shutter. By adhering first sheet 20 to the face of the louver panel 52, and adhering the second sheet 30 to the face of the tilt rod 54 adjacent the panel 52, quick reconnection of the louver to the rod may be provided.

It should be understood that the links 18, 20 of the embodiments of FIGS. 1-3 may be made of almost any sturdy material that permits application of a meaningful amount of force with breaking. The adhesive should also be strong enough to withstand the shear forces applied to the sheets 20, 30 when the rod is moved vertically, drawing the louver panels into a close and/or open position. It is contemplated that other means of adhering the first and second components to respective devices may be used, including a Velcro® connector, or a mechanical device such as a threaded screw.

It should also be appreciated that the system 10 can be taken apart and put back together as desired. By pinching each link inwardly, the link may be withdrawn from the opening in the sheet. This way, the first and second links may be detached by the user or reattached when applied to devices to be joined. Of course, some embodiments may have links configured so as not to be easily disengaged from each other or from the sheets, or permanently engaged to each other and/or the sheets. In an alternative embodiment, each link comprises a closed ring engaged to each other and to their respective sheets so that no disengagement is possible. The rings may be engaged to the sheets by securing a thin rod or plate to the first sheet and positioning the rod or sheet within one of the rings, with a second rod or plate on the second sheet positioned similarly to achieve the same movable engagement as other embodiments described herein.

As may be appreciated, numerous other arrangements of coupling mechanisms and board surfaces are contemplated by the present invention. For example, if so desired, the first and second links may be configured to permit continuous rotation of one link relative to the other so that one device may spin relative to another device where both devices are connected using an embodiment of the present invention. The present invention is not limited by the disclosed and described embodiments but is rather reflected in the full scope of the claims presented herein and as properly interpreted by persons of ordinary skill in the art.

What is claimed is:

1. A system for joining two components of a louvered shutter together, the system comprising:

a first connector comprising a first link connected to a first resilient sheet, the first sheet comprising an outer side configured to be wrapped over a surface of a louver panel, the first sheet further comprising an adhesive material on the outer side thereof for securing the first sheet to the surface of the louver panel; and a second connector comprising a second link connected to a second resilient sheet, the second sheet comprising an outer side configured to be wrapped over a surface of an actuation rod, the second sheet further comprising an adhesive material on the outer side thereof for securing the second sheet to the surface of the actuation rod;

wherein the first and second sheets each comprise an opening passing therethrough, the opening defining an opening width; and wherein the first and second links each comprise an upper portion and a lower portion, the upper portion defining a generally U-shaped section, and the lower portion defining two tabs, each tab connected to, and extending outwardly from, a respective end of the U-shaped section;

wherein the upper portions of the first and second links define a width smaller than the opening width, and the lower portions of the first and second links define a width larger than the opening width, such that inserting the upper portions of the first and second links through the openings of the first and second sheets, respectively, abuts the lower portions of the first and second links against the outer sides of the first and second sheets, respectively; and wherein the upper portions of the first and second links are interlocked in a manner that permits movement of the first connector relative to the second connector so that when the first connector is connected to the louver panel and the second connector is connected to the actuation rod, the louver panel and actuation rod are joined together so that movement of one may drive movement of the other.

* * * * *